United States Patent [19]

Koga

[11] Patent Number: 5,701,362
[45] Date of Patent: Dec. 23, 1997

[54] WIRE BREAKAGE DETECTING METHOD

[75] Inventor: Hiromi Koga, Chikugo, Japan

[73] Assignee: Rohm Co., Ltd., Kyoto, Japan

[21] Appl. No.: 498,838

[22] Filed: Jul. 6, 1995

[30] Foreign Application Priority Data

Jul. 8, 1994 [JP] Japan ................ 6-157462

[51] Int. Cl.$^6$ ............ G06K 9/00; H04N 7/18; H04N 9/47
[52] U.S. Cl. ............ 382/149; 348/126; 250/559.4
[58] Field of Search ............ 382/141, 145–152; 348/86–87, 94–95, 125–126; 250/559.34, 559.42, 559.43, 559.4

[56] References Cited

U.S. PATENT DOCUMENTS

| | | | |
|---|---|---|---|
| 5,238,173 | 8/1993 | Ura et al. | 228/104 |
| 5,412,742 | 5/1995 | Takasaki et al. | 382/316 |
| 5,424,838 | 6/1995 | Siu | 356/394 |
| 5,574,800 | 11/1996 | Inoue et al. | 382/149 |

*Primary Examiner*—Leo Boudreau
*Assistant Examiner*—Bhavesh Mehta
*Attorney, Agent, or Firm*—Nikaido Marmelstein Murray & Oram LLP

[57] ABSTRACT

A wire breakage detecting method, being a method of detecting breakage of wire bonded on a chip of an electronic component by image processing, includes the step of observing a point of the wire as a pixel of one color of binary images of black and white, observing while rotating plural pixels around the present observation pixel being observed in a specific direction, moving the observation point of the wire by detection of the pixel of the same color as said color of the binary images, moving the observation point continuously, and detecting breakage of wire by inversion of the moving direction of the observation point.

4 Claims, 6 Drawing Sheets

WIRE BREAKAGE DETECTING METHOD

BACKGROUND OF THE INVENTION

The present invention relates to a detecting method of breakage of a wire bonded on a chip of an electronic component. More particularly, it relates to a method of detecting breakage of a wire by the change of moving direction of observation point, by displaying the chip and bonded wire as binary images of black and white, and moving the observation point on the wire.

Herein, the wire refers to any metal wire used in electrical connection between an electrode pad of an electronic component chip and a lead frame.

As a method of detecting breakage of a wire bonded to a chip of a tiny electronic component such as semiconductor chip and electrolytic capacitor, a method of detecting by image processing has been studied. In this method, for example as shown in FIG. 6, detection start points b1, b2, b3, ..., bn are determined at specific y-coordinates parallel to the x-axis, and at y-coordinates larger than the y-coordinates of the highest position of the wire, and moreover the interval of the detection start points b1, b2, ... are determined at a specific interval, and the y-coordinates of the observation points are lowered from each detection start point parallel to the y-axis direction until a black pixel is detected (in positioning of detection start point, the relation of the x-axis and y-axis my be reverse). If black pixel is not observed by lowering the observation point sequentially downward, the y-coordinate becomes 0, detection work is suspended, and breakage is determined (when x-coordinate corresponds to point "bn" in FIG. 6).

The interval of the detection start points b1, b2, ... is set at about 1 pixel.

In this method of detecting wire breakage, when the wire direction is the same as the detecting direction (in this case, direction parallel to the y-axis), or nearly the same as the detecting direction on the screen if the wire is inclined only by less than 1 pixel, only the end closest to the detection start point is detected, and broken portion cannot be detected.

The invention is intended to solve such problem, and it is an object thereof to present a wire breakage detecting method capable of detecting breakage accurately by image processing regardless of the wire direction.

SUMMARY OF THE INVENTION

To achieve the object, the invention provides a wire breakage detecting method, being a method of detecting breakage of wire bonded on a chip of an electronic component by image processing, comprising:

observing a point of the wire as a pixel of one color of binary images of black and white, observing while rotating plural pixels around the present observation pixel being observed in a specific direction, moving the observation point of the wire by detection of the pixel of the same color as said color of the binary images, moving the observation point continuously, and detecting breakage of wire by inversion of the moving direction of the observation point.

Preferably, the rotating direction of rotating plural pixels around the present observation pixel in a specific direction counterclockwise rotation when starting observation from the right end side of the chip, and clockwise rotation when starting observation from the left end side of the chip, and therefore the observation point can be moved in the wire directly securely from the detection start point.

Further preferably, plural pixels around the present observation pixel are rotated in a specific direction to return the observation start pixel for observing from the present observation pixel to the previous observation pixel, thereby moving from the previous observation pixel to the adjacent pixel either clockwise or counterclockwise, and therefore the measurement start point can be determined in a specific relation, so that the observation point can be detected securely.

According to the wire breakage detecting method of the invention, since a pixel (for example, a black pixel) capable of detecting the wire is detected while sequentially rotating the plural pixels around the wire observation pixel, the observation point can be securely moved along the wire regardless of the wire direction, making a U-turn where the wire is broken, and hence the moving direction of the observation point is inverted. As a result, by inspecting the moving direction of the observation point, the breakage can be detected securely.

DETAILED DESCRIPTION

Figure 1:
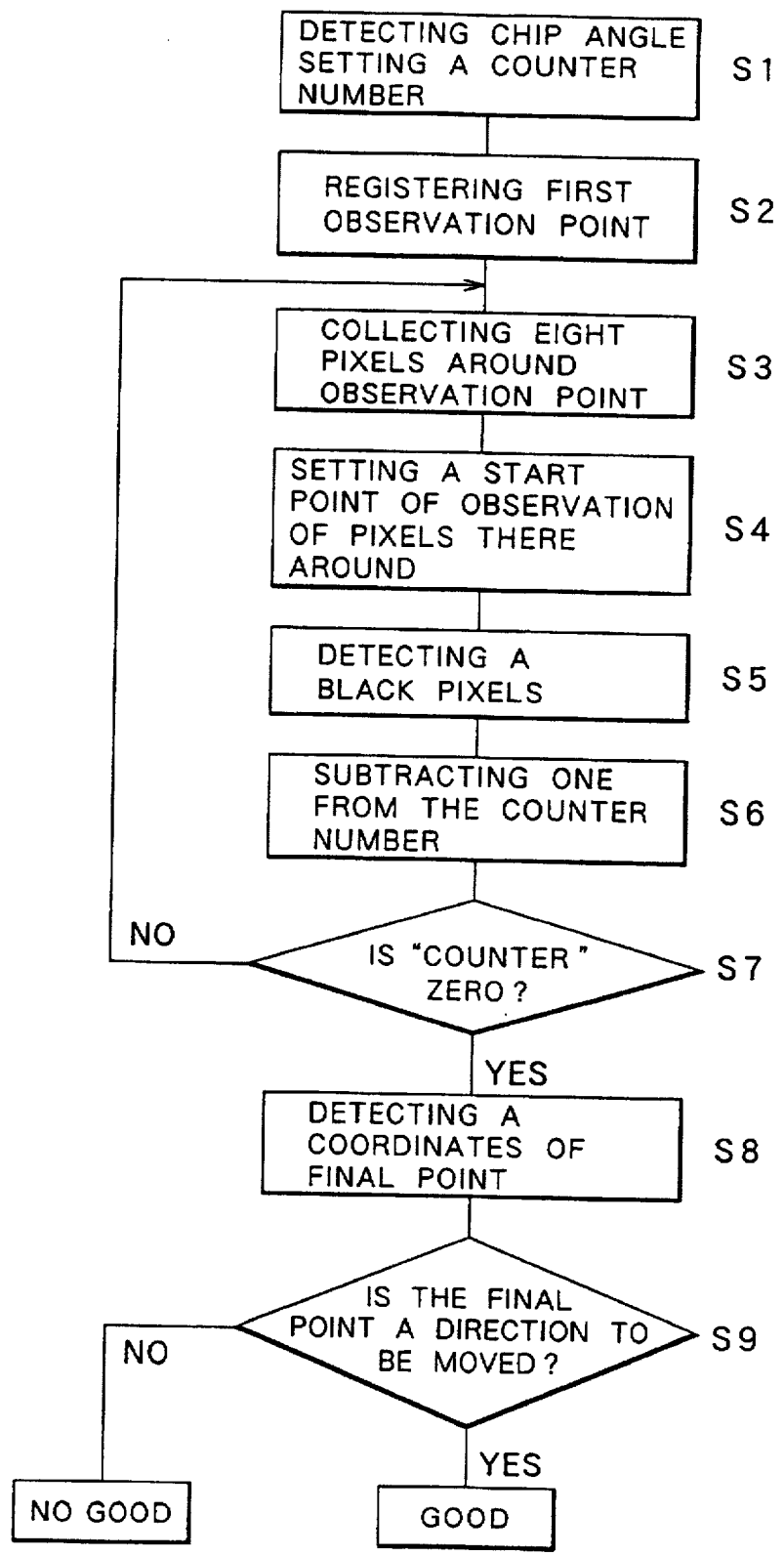
FIG. 1 is a flow chart showing an embodiment of wire breakage detecting method of the invention.

Referring now to the drawings, the wire breakage detecting method of the invention is described below.

Figure 2:
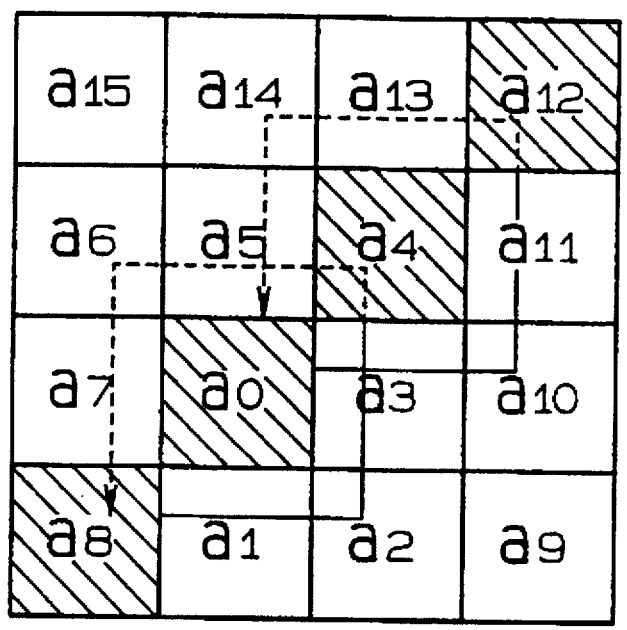
FIG. 2 is a schematic magnified view showing an example of image data as pixels.
Figure 3:
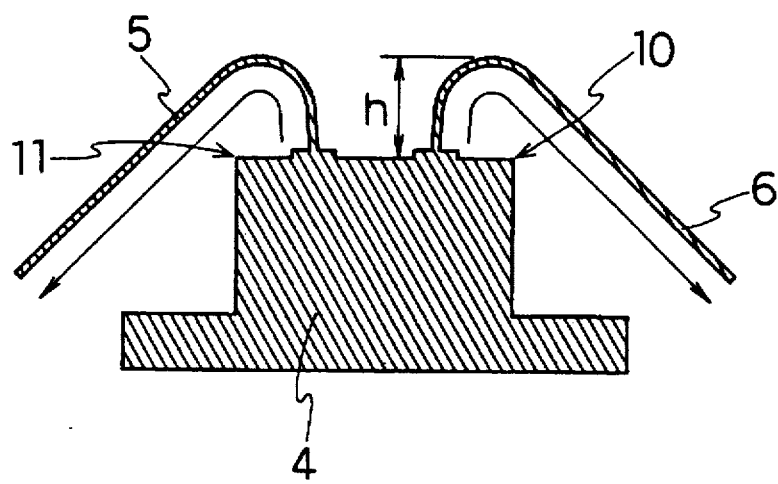
FIGS. 3(a) and 3(b) show semiconductor chip containing wires of the invention as seen in a binary image taken by a CCD camera from a lateral direction.
Figure 3:
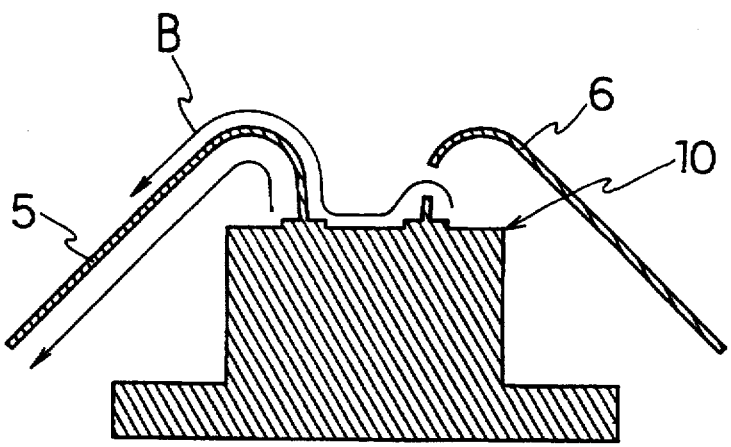

FIG. 1 is a flow chart for explaining an embodiment of wire breakage method of the invention, and FIG. 2 is a schematic magnified view showing image data as pixels, in which a0 to a15 denote pixels, and shaded pixels a0, a4, a8, and a12 are black pixels indicating, for example, the position of chip or wire, and other pixels are white pixels indicating a free space not occupied by chip or wire. FIG. 3 shows a lateral view of a semiconductor chip 4 bonded with wires as taken by a CCD camera, showing data of binary images of black and white, for example, taken as a white pixel when data is 1 and as a black pixel when data is 0, in which wires 5, 6 are extended to the right and left side and each end is bonded to a lead frame or the like. At this time, the configuration of pixels is recognized by the coordinates (x, y) of row and line, from the origin (0, 0) defined at a proper position. In the invention, by tracing the black pixel indicating the presence of chip or wire, the observation point is moved along the wires 5, 6, and the change of the moving direction of the observation point is detected, thereby detecting breakage of wire.

Referring back to FIG. 1, an embodiment of wire breakage detecting method of the invention is described below. First, at S1, the chip angle 10 of the semiconductor chip 4 is detected, and the counter number is set according to the wire length 5 or 6. This chip angle 10 is registered to be at the right end or left end (S2). At S3, data is collected to determine whether the eight pixels around the observation point are white or black. A start point is set to determine which one of the eight pixels around the observation point is observed in the first place (S4), and a black pixel is detected (S5).

The observation direction of eight pixels around the observation point is preferably counterclockwise rotation about the pixels when the first observation point is at the right end side of the chip, and clockwise rotation about the pixels when the first observation point is at the left end side. The reason is as follows:

When the black pixels are sequentially observed from the right end side, the observation point moves sequentially to the left side, and the move of the observation point to the first observed black pixel is straight without loss, securely moving on the wire, so that counterclockwise rotation is preferred. If the first observation point at the left end side, the relation is reverse, and it preferred to rotate clockwise.

Figure 4:
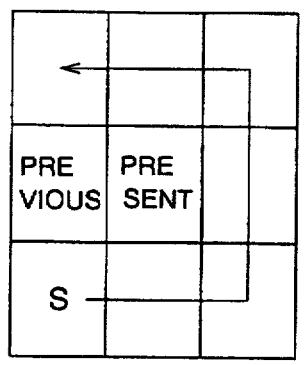
FIG. 4 is a diagram showing the sequence of observing pixels around the present observation point in order to move the observation point on the wire.
Figure 4:
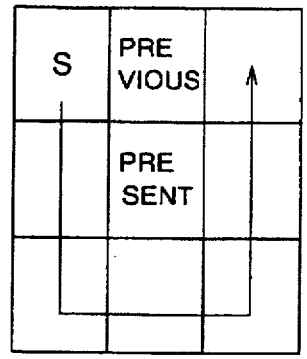
Figure 4:
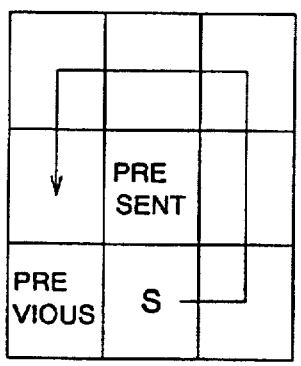
Figure 4:
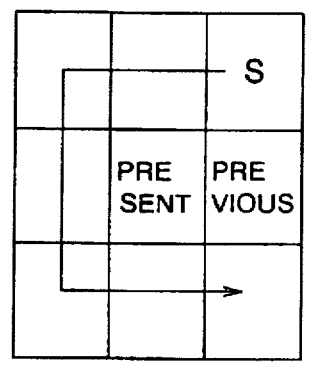
Figure 4:
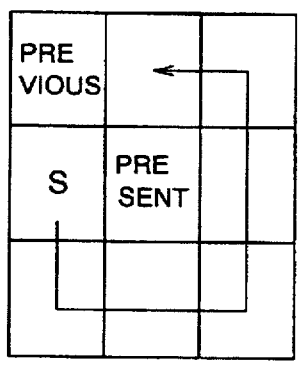
Figure 4:
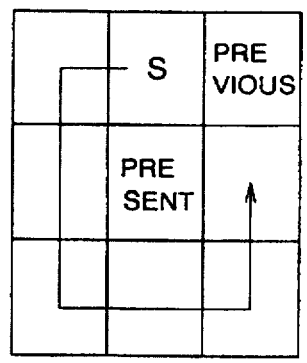
Figure 4:
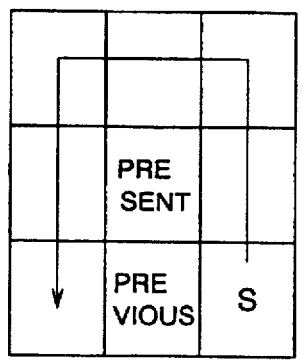
Figure 4:
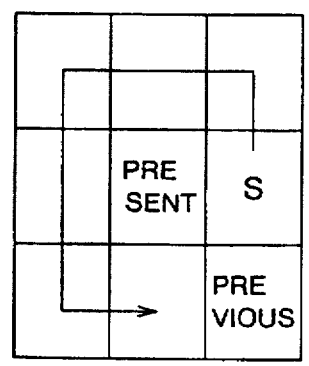
Figure 5:
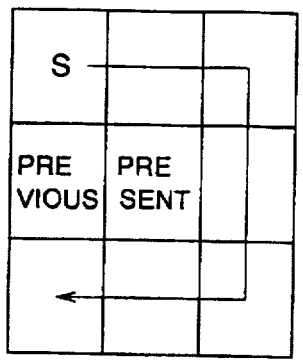
FIG. 5 is a diagram showing the sequence of observing pixels around the present observation point in order to move the observation point on the wire.
Figure 5:
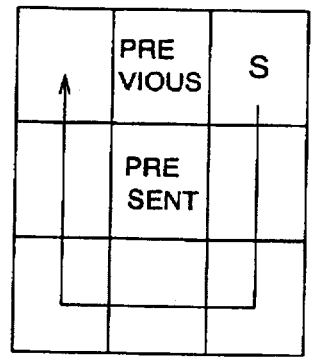
Figure 5:
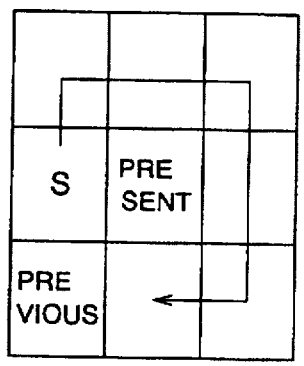
Figure 5:
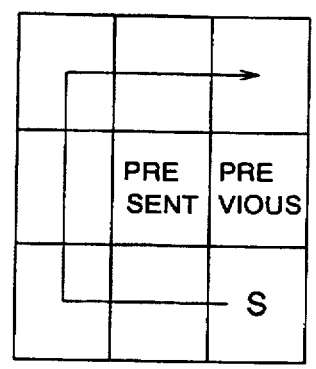
Figure 5:
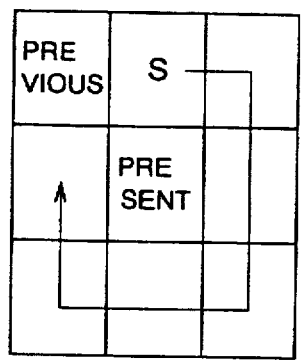
Figure 5:
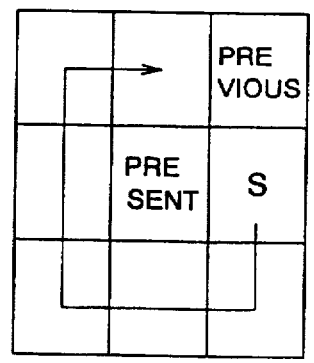
Figure 5:
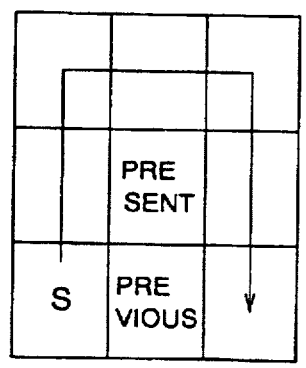
Figure 5:
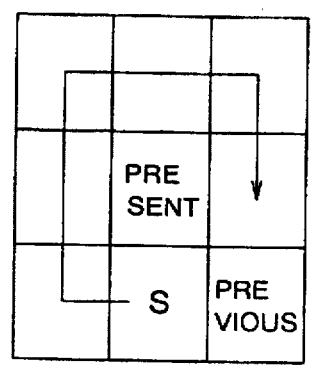
Figure 6:
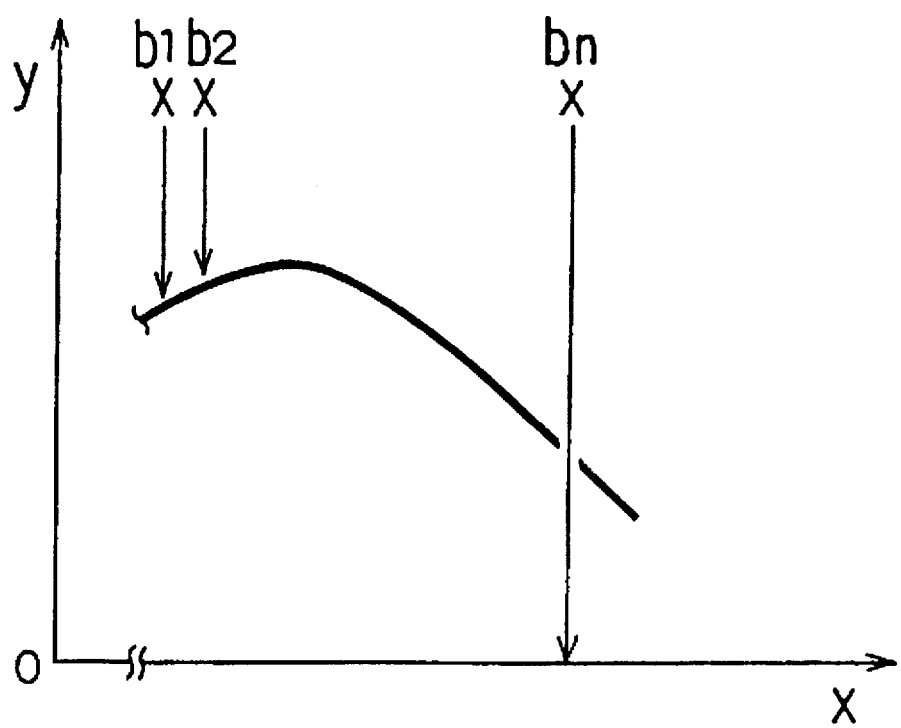
FIG. 6 is a diagram showing an example of conventional wire breakage detecting method.

To set to start observation from which one of the surrounding pixels, for example as shown in FIGS. 4 and 5, returning from the present observation point (pixel indicated by "present" in FIGS. 4, 5) to the previous observation point (pixel indicated by "previous" in FIGS. 4, 5), the observation start pixel is the pixel (pixel indicated by S in FIG. 4, 5) adjacent to the previous observation point in the clockwise or counterclockwise direction. That is, FIG. 4 shows a case of detection of black pixel from the right end 10 side of the chip 4, returning from "present" pixel to "previous" pixel, the pixel adjacent to the "previous" pixel counterclockwise is the detection start pixel S. FIG. 5 shows the case of detection of black pixel from the left end 11 side of the chip 4, returning from the "present" pixel to "previous" pixel, the pixel adjacent in the clockwise direction is the detection start pixel S.

Observing, the pixels sequentially, a black pixel is detected (S5). When a black pixel is detected, observation of surrounding pixels is stopped, and a newly found black pixel is registered as a new observation point. Explaining this mode by referring to FIG. 2, supposing the previous observation point to be a8 and the present observation point to be a0, returning from pixel a0 to pixel a8, pixel a1 adjacent couterclockwise is the start point, and a2, a3, a4 are detected while rotating couterclockwise, and if a4 is a black pixel, observation is suspended at a4, and a4 is a new observation point. Consequently, the counter number is decreased by one (S6), and it is determined whether the counter number has become 0 or not (S7), and unless 0, returning to S3, the same process is repeated. If 0, the coordinates of the final point are detected (S8). Supposing the counter is not 0, the step returns to S3 to detect next black pixel. At step S4, returning from a new observation point a4 to the previous observation point a0, one pixel advanced counterclockwise from the previous observation point a0, that is, pixel a3 is the observation start point (when the observation start point is at the left end side, the pixel a5 one step advanced clockwise from the previous observation point a0 is the detection start point). All of pixels a3, a10, a11 are white pixels, and hence the observation point is sequentially moved to a3, a10, and a11. At pixel a12, when the data is found to be a black pixel, detection is suspended at a12. The steps after S6 are the same as mentioned above. When returning to step S5 after S7, the information of a8 before the previous observation point a0 is discarded, and pixel a4 is registered as previous observation point, and a new observation point is a12. When the counter becomes 0, the coordinates of the pixel of the final point are detected (S8), and it is determined if the final point is the moving direction to be moved or not (S9). The advancing direction of observation point of a conforming piece indicated by arrow in FIG. 3 (a), and that of a defective piece in FIG. 3 (b), and the final point is indicated by the arrow head. Actually, the observation points are pixels, and the arrow should overlap the wires 5 and 6, but herein it is drawn along the wiring for the sake of explanation. When the wire is free from breakage, the detection start point and observed final point coincide with the end of the detection start point side of the wire as shown in FIG. 3 (a), and if the wire is broken, as indicated by arrow B in FIG. 3 (b), the observation point advances in the opposite direction of the observation start point (the right end of the chip) of the semiconductor chip 4. Hence, the observed final point does not coincide with the observation start point 10 side, hence indicating the presence of breakage.

In the embodiment described herein, pixels to be observed around the observation point are eight pixels, but the observation point my not be always one pixel, but two or more pixels may be observed when the wire is thick, and in such a case the number of pixels to be observed in the surrounding will be more than eight.

Thus, according to the breakage detecting method of the invention, it is not necessary to check breakage of wiring by a monitor or the like, and wire breakage can be found automatically and accurately.

By employing the embodiment, moreover, the maximum height of the wires 5, 6 from the surface of semiconductor chip 4, or the maximum value of the distance from the surface of semiconductor chip 4 to the wires 5, 6 may be determined also as shown in FIG. 3.

In this way, according to the wire breakage detecting method of the invention, breakage of bonded wire can be detected securely, and defective pieces will not be mixed in and the yield is improved, and above all detection is automatic, so that-the detection cost may be curtailed.

Besides, since the observation point moves continuously on the wire, wire breakage can be detected securely without being affected by screen noise as experienced in a detecting method by means of a monitor.

Though several embodiments of the present invention are described above, it is to be understood that the present invention is not limited only to the above-mentioned, various changes and modifications may be made in the invention without departing from the spirit and scope thereof.

What is claimed is:

1. A wire breakage detection method for detecting breakage of a wire bonded on a chip of an electronic component by image processing comprising the steps of:
   a) detecting a chip angle and setting a counter number according to a wire length;
   b) setting first observation point;
   c) collecting plural pixels around said observation point;
   d) setting a start point of observation of the plural pixels around said observation point;
   e) observing pixels sequentially in a specific direction around said observation point starting at said start point;
   f) determining whether said pixels are white or black;
   g) subtracting one from the counter number when a black pixel is determined;
   h) determining if the counter is zero (0);
   i) repeating the above steps starting with c) if the counter is not zero (0);

j) if the counter is zero (0), detecting coordinates of the final observation point;

k) if the first and final observation points coincide, outputting an indication that no wire is broken; and l) if the first and final observation points do not coincide, outputting an indication that a wire is broken.

2. The wire breakage detecting method of claim 1, wherein the step of observing pixels sequentially in a specific direction is a counterclockwise rotation when observation is started from a right end side of the chip, and a clockwise rotation when observation is started from a left side of the chip.

3. The wire breakage detecting method of claim 2, wherein the step of setting a start point of the plural pixels around the observation point are rotated in a specific direction to return the start point from a present observation pixel to a previous observation pixel, therein moving from the previous observation pixel to an adjacent pixel either clockwise or counterclockwise.

4. The wire breakage detecting method of claim 1 wherein the number of plural pixels collected around the observation point are eight pixels.

* * * * *